(12) United States Patent
Astorga-Wells

(10) Patent No.: US 8,237,117 B2
(45) Date of Patent: Aug. 7, 2012

(54) METHODS AND INTERFACES FOR SINGLE AND MULTIDIMENSIONAL SEPARATIONS FOR CHARACTERIZATION AND/OR IDENTIFICATION OF MOLECULES BY MASS SPECTROMETRY

(75) Inventor: Juan Astorga-Wells, Skarpnack (SE)

(73) Assignee: PerkinElmer Health Sciences, Inc., Waltham, MA (US)

( * ) Notice: Subject to any disclaimer, the term of this patent is extended or adjusted under 35 U.S.C. 154(b) by 0 days.

(21) Appl. No.: 13/038,012

(22) Filed: Mar. 1, 2011

(65) Prior Publication Data

US 2011/0297822 A1    Dec. 8, 2011

Related U.S. Application Data

(63) Continuation of application No. 11/792,689, filed as application No. PCT/SE2005/001844 on Dec. 6, 2005, now Pat. No. 7,902,500.

(30) Foreign Application Priority Data

Dec. 6, 2004 (SE) ........................ 0402966

(51) Int. Cl.
*B01D 61/44* (2006.01)
*H01J 49/04* (2006.01)
(52) U.S. Cl. ........ 250/288; 204/453; 204/542; 204/554; 204/601
(58) Field of Classification Search ................. 250/281, 250/282, 288; 204/451, 453, 542, 545, 554, 204/601
See application file for complete search history.

(56) References Cited

U.S. PATENT DOCUMENTS 5,505,832 A    4/1996   Laukien et al.
6,396,057 B1   5/2002   Jarrell et al.

(Continued)

FOREIGN PATENT DOCUMENTS

WO    WO 2004/056697    7/2004

(Continued)

OTHER PUBLICATIONS

Buryakov, et al., "A new method of separation of multiatomic fans by mobility at atmospheric pressure using a high-frequency amplitude-asymmetric strong electric field," Int. J. of Mass Spectrometry and Ion Processes, 128(3):143-148, (1993).

(Continued)

*Primary Examiner* — Bernard E Souw
(74) *Attorney, Agent, or Firm* — Fish & Richardson P.C.

(57) ABSTRACT

The present invention relates a use of the electrocapture-based separation technology combined with mass spectrometrical fragmentation methods, e.g. sequence of polypeptides by collision-induce dissociation mass spectrometry, for the identification and/or characterization molecules of interest. It also relates the combination of the electrocapture-base separation technology with other liquid separation methods, as e.g. liquid chromatography, in order to achieve multidimensional separations prior mass spectrometrical analysis. In addition, it relates physical interfaces between electrocapture-based separations and different types mass spectrometers for on-line or off-line analysis, as well as the coupling of electrocapture-based separations, liquid chromatography and different types of mass spectrometers.

22 Claims, 4 Drawing Sheets

U.S. PATENT DOCUMENTS

| | | | |
|---|---|---|---|
| 6,831,271 | B1 | 12/2004 | Guevremont et al. |
| 7,731,827 | B2 * | 6/2010 | Astorga-Wells et al. ..... 204/451 |
| 7,902,500 | B2 * | 3/2011 | Astorga-Wells .............. 250/288 |
| 2003/0150987 | A1 | 8/2003 | Guevremont et al. |
| 2003/0201390 | A1 | 10/2003 | Corso et al. |
| 2004/0041093 | A1 | 3/2004 | Schultz et al. |
| 2004/0072337 | A1 | 4/2004 | Moon et al. |
| 2005/0284762 | A1 | 12/2005 | Laukien et al. |
| 2006/0145071 | A1 | 7/2006 | Frazer et al. |
| 2006/0263904 | A1 | 11/2006 | Morozov et al. |

FOREIGN PATENT DOCUMENTS

| | | | |
|---|---|---|---|
| WO | WO2004/056697 | A1 * | 7/2004 |

OTHER PUBLICATIONS

Astorga-Wells et al., "A Microfluidic Electrocapture Device in Sample Preparation for Protein Analysis by MALDI Mass Spectrometry", Analytical Chemistry, vol. 75, pp. 5213-5219 (2003).

Astorga-Wells, "Microfluidic Electrocapture Technology in Protein and Peptide Analysis," Thesis: From the Department of Medical Biochemistry and Biophysics Karolinska Institute, Stockholm, Sweden, 2004.

Supplementary European search report for corresponding EP Application No. 05813450.3, dated Oct. 21, 2010.

* cited by examiner

METHODS AND INTERFACES FOR SINGLE AND MULTIDIMENSIONAL SEPARATIONS FOR CHARACTERIZATION AND/OR IDENTIFICATION OF MOLECULES BY MASS SPECTROMETRY

CROSS-REFERENCE TO RELATED APPLICATIONS

This application is a continuation of U.S. Ser. No. 11/792,689, filed on Jun. 6, 2007, now U.S. Pat. No. 7,902,500, which is the national phase of International Application PCT/SE05/01844, filed Dec. 6, 2005. PCT/SE05/01844 claims the priority of SE 0402966-6, filed on Dec. 6, 2004.

BACKGROUND

The present invention represents a novel mode to utilize a device described in PCT/SE2003/002027, which has been published as WO 2004/056697, the entire contents of which are incorporated herein by reference (see FIG. 1 and Abstract). The key innovative steps in this invention are:

Methods and interfaces for the combination of electrocapture-based separations (described in PCT/SE2003/002027, WO 2004/056697) with mass spectrometry for characterization and/or identification of molecules of interest. Mass spectrometry (MS) is a powerful analytical tool for the identification and characterization of peptides, proteins, DNA, RNA, drugs, other polymers and small molecules. Even though MS can analyze samples containing more than one particular type of molecules, a separation step is usually necessary when analyzing a sample having a complex mixture of molecules. This is particularly true for samples derived from biological sources such as for example, blood, urine, saliva, cell extracts or fractions, bacteria extracts or fractions. Another important application where a separation step is necessary before MS analysis is in the identification of proteins via the enzyme digestion (e.g., trysin digestion) of a single protein (or a mixture of proteins) and the following separation and injection into the mass spectrometer. In this case peptides are separated and injected into the mass spectrometer, in which one peptide with a particular mass and charge ratio (m/z) is selected for fragmentation followed by tandem mass spectrometry (MS/MS). Utilizing MS/MS, the m/z value of the fragments are determined, thus making the determination of the amino acid sequence of the particular peptide possible, in order to identify the protein from which the peptide was derived (via database search). For all these mixtures of molecules, the separation step improves the performance of the overall analysis by mass spectrometry (higher number of molecules are characterized and/or identified with increased sensitivity).

SUMMARY

The connection of the electrocapture based separation with mass spectrometry is not a trivial-issue, since molecules need to be both ionized and in the gas-phase in order to be injected into the mass spectrometer.

The separation with the electrocapture device must be performed in solution (molecules are dissolved in a particular solvent), thus a particular interface and method should be developed to combine this two techniques.

In addition, another critical issue is that the interface (or connection) between both technologies must be done without disrupting the separation process.

One of the innovative steps described in this application is to combine electospray ionization mass spectrometry (ESI-MS) with the electrocapture device to separate molecules of interest. In electrospray ionization, molecules are ionized and transferred to the gas-phase by applying an electric field (about 1000 and 3000 kV) between the solution, where the molecules of interest are dissolved, and the mass spectrometer. Not all aspects of electrospray ionization are fully understood, but it is known that electrostatic-repulsion and solvent characteristics (evaporation, surface tension and pH) play an important role. In brief, the difference of electric potential between the solution and the mass spectrometer induces the formation of the electrospray, which involves the formation of micrometer and nanometer size droplets (due to an electrostatic effect) that have the same charge. The latter causes the droplets to be repelled from one another (due to charge-to-charge repulsion). In parallel to this process, the solvent of the droplets starts to evaporate, and together with electrostatic repulsion, allow the molecules to be transferred to the gas-phase in an ionized state.

It is clear from the above that the electric potential between the solvent and the mass spectrometer must be applied during the electrospray ionisation-mass spectrometry (ESI-MS) analysis. It is here where problems arise from the connection of the capture device with ESI-MS. The capture device has at least two electrodes by which the molecules are captured and separated. For this reason, the voltage from the ESI must not interfere with the voltage in the capture device (and vice-versa). Therefore, if a proper voltage decoupling is not achieved, the electrospray process and/or the operation of the capture device will deteriorate to the extent that molecules are not separated/captured on the capture device and/or the electrospray process is not completed.

The decoupling is achieved by the use of a capillary having micrometer-sized dimensions (between 5 to 150 μm), and/or the use of buffers of low conductivity (using solutions of low salt concentration (e.g., between 1-20 mM and/or the use of solutions with organic solvents (e.g., acetonitrile, methanol) in a concentration between 99% to 1%) and/or the utilization of a capture device circuit voltage where the power supply of the capture device is electrically floating and thus does not interfere with the electrospray voltage. In addition, the decoupling can be achieved by using a sheath flow interface in which the electrospray voltage is applied to the electrospray solvent that travels coaxially to the outlet of the device, and is helped by a further coaxial flow of gas (sheath flow interfaces are generally known in the art and are for example described in the literature (e.g., Electrophoresis 2004, 25, 1927-1948)).

Another innovative step is the combination of electrocapture-based separations and chromatography separations with mass spectrometry. In addition to the connection of the electrocapture device with electrospray ionization mass spectrometry, a step to further separate the molecules is to combine the electrocapture-based separation with a chromatography process (e.g., reverse phase chromatography) in order to carry out multidimensional separations. In this manner, the separation power of the electrocapture-based separations can be increased, resulting in an improvement of the performance of the MS measurements (higher number of molecules characterized and/or identified with increased sensitivity). The most common manner to perform multidimensional separation prior to mass spectrometry is by combining ion-exchange chromatography (where the separation is based on charge) with reverse-phase chromatography (where the separation is based on hydrophobicity). The main problem with this approach is that the ion-exchange chromatography needs salts to separate the molecules of interest. Salts can be detrimental to the mass spectrometer. Thus, ion-exchange chromatography and reverse-phase chromatography cannot be connected online, hindering the automation of the overall separation procedure. The electrocapture-based separations is a method that separates molecules according to their electrophoretic mobility and does not use salts, making a straightforward connection to reverse-phase chromatography for multidimensional separation prior to mass spectrometry possible.

DETAILED DESCRIPTION

Figure 1:
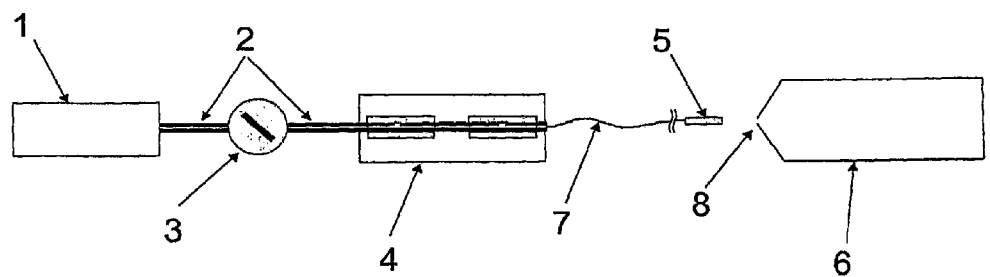
FIG. 1 shows an embodiment of a mass spectrometer integrated with an electrocapture device.

FIG. 1 shows an embodiment according to the invention. Reference FIG. 1 denotes a pump, 2 denotes fluidic connectors (pump injector-capture device), 3 denotes an injector, 4 denotes a capture device (see FIG. 1 and Abstract of incorporated PCT reference WO2004/056697 A1, 5 denotes an electrospray interface-source, 6 denotes a mass spectrometer, 7 denotes a fluidic connector (capture device-electrospray source) and 8 denotes the inlet of the mass spectrometer.

Figure 2:
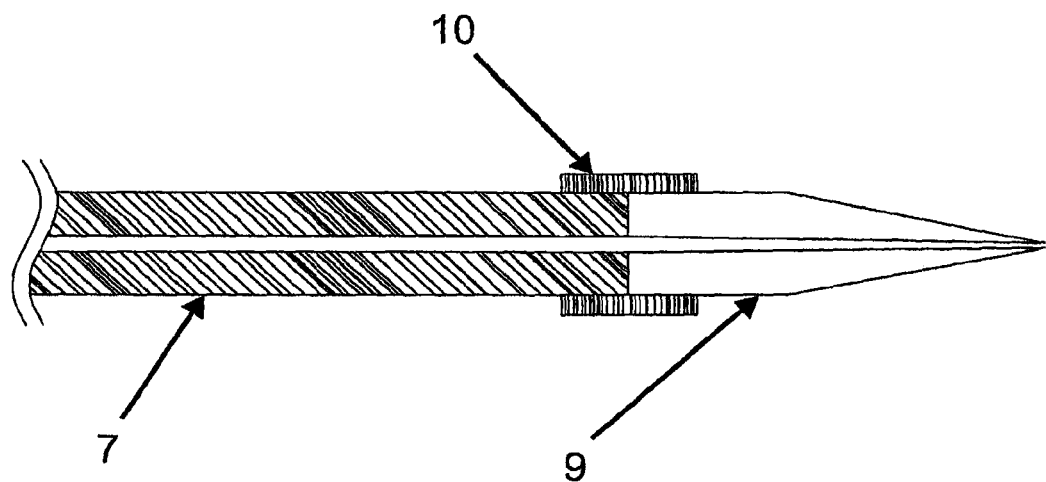
FIG. 2 shows an embodiment of the electrospray interface-source.

FIG. 2 shows details of the electrospray interface-source 5 of FIG. 1 wherein 9 is a tip coated with a conductive material and 10 is a connector with (zero or low dead volume).

Figure 3:
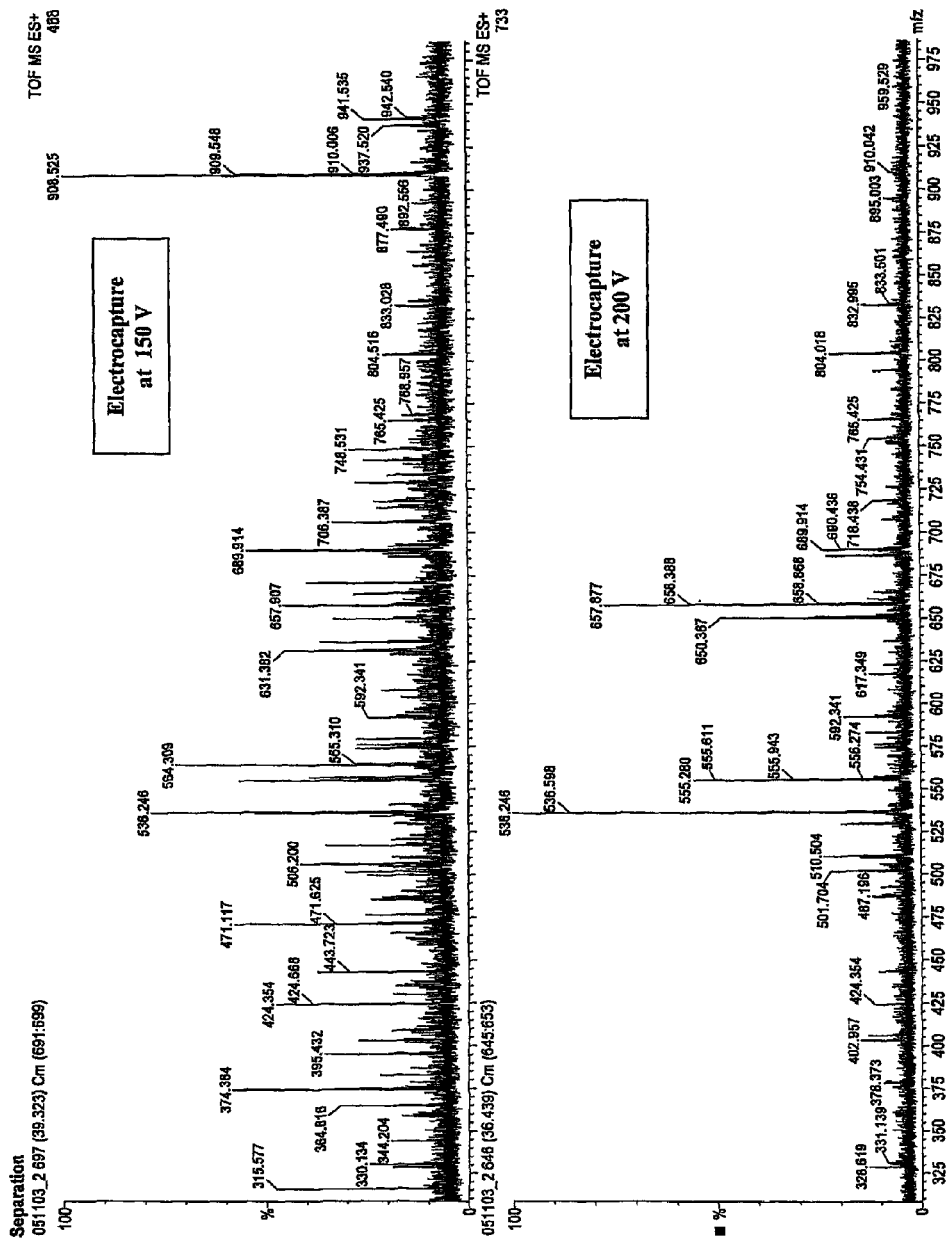
FIG. 3 shows ESI-mass spectra obtained when electrocapture-based separation is used.

FIG. 3 shows on-line electrocapture-based separations and ESI-Mass Spectra. The system setup includes a 1 μL-injector, a syringe pump, a power supply, an electrocapture device and a 50 μm fused silica capillary (20 cm) that connects the outlet of the electrocapture device to the electrospray source. The source is a silica capillary coated with a conductive material (for reference, see FIGS. 1 and 2), and the mass spectrometer is a Q-T of flight mass spectrometer. Peptides obtained from the trypsin digestion of 4 proteins (BSA, myoglobin, ADH and cytochrome C) dissolved in 10 mM $NH_4HCOO$ (pH 5.5 and 20% acetonitrile) are captured using an initial voltage drop of 300 V and a flow rate of 0.2 μL/min. As seen in the figure above, different peak profiles can be seen in the ESI-MS spectra by using different electrocapture voltages (200 and 250 V), showing that the electrocapture device can be coupled online to ESI-MS to fractionate molecules of interest.

Figure 4A:
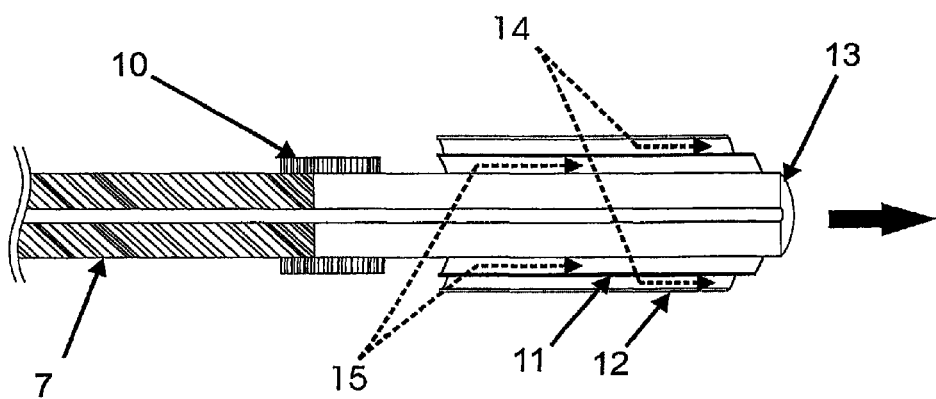
FIG. 4 shows an embodiment of the sheath flow interface.
Figure 4B:
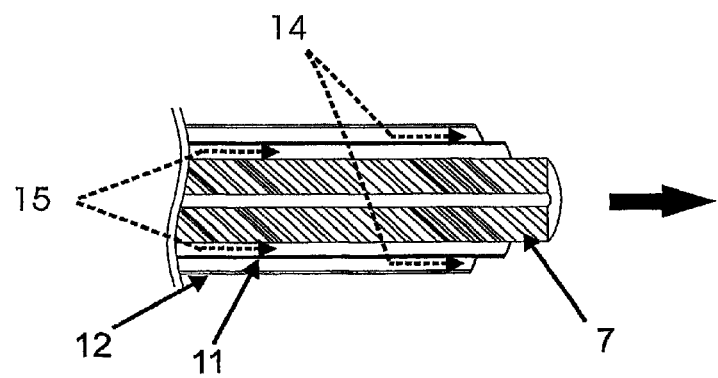

FIG. 4 shows a sheath flow interface for the connection of the electrocapture device with an electrospray ionization mass spectrometer. The figure shows two different embodiments of the interface (A and B). The sheath flow interfaces allow decoupling between the electrocapture device and electrospray voltages. In FIG. 4A the item 11 depicts an electrically conductive tube from which the electric field for the electrospray process is applied. An electrolyte solution is continuously flowing (pumped) in conductive tube 11. Item 12 depicts a tube in which a gas is continuously flown through. The gas (sheath gas, item 14) and the electrolyte (sheath liquid, item 15) are travelling coaxial to a capillary tube (13) preferably made of silica and connected to fluidic connector (7). FIG. 4B depicts another setup to decouple the voltages, here the item 11 depicts an electrically conductive tube from which the electric field for the electrospray process is applied. In conductive tube (11) an electrolyte solution is continuously flowing (pumped). Item 12 depicts a tube where a gas is continuously flown through. The gas and the electrolyte are travelling coaxial to the fluidic connector (7). The arrow shows the direction to a mass spectrometer.

The invention also relates to a separation device featuring a capture device, a fluidic connector e.g., an electrospray source, an electrospray interface-source and a mass spectrometer. The electrospray interface-source may be a conductively coated tip connected to at least one connector. The conductive layer is made of any electrically conductive material such as a metal e.g., silver or gold. One or more chromatographic columns capable of separating molecules by size or hydrophobicity could be placed before or after the electrocapture device.

All specifications regarding materials and performance apply mutatis mutandis to both the methods and the devices according to the invention.

The invention claimed is:

1. An apparatus, comprising:
    at least one channel formed in an electrically non-conductive material;
    at least one inlet and for the flow of an electrolyte medium into the channel and at least one outlet for the flow of the electrolyte medium from the channel;
    at least two electrodes each comprising a conductive membrane, the two electrodes being individually separated from the channel and in electrical contact with the electrolyte medium, where the conductive membranes permit the passage of certain charged ions and charged molecules and block other charged ions and charged molecules;
    an electrospray source comprising a tip; and
    an interface connecting the at least one channel and the electrospray source,
    wherein the interface comprises a sheath-flow interface.

2. The apparatus of claim 1, wherein the interface comprises a capillary tube.

3. The apparatus of claims 2, wherein the capillary tube is a small bore capillary tube.

4. The apparatus of claims 2, wherein the capillary tube is a fused silica capillary tube.

5. The apparatus of claim 1, wherein the interface comprises a capillary tube between the at least one channel and the electrospray source.

6. The apparatus of claim 1, wherein the interface comprises a capillary tube connected to a tip, the tip being coated with an electrically conductive material.

7. The apparatus of claim 1, wherein the interface comprises a tip coated with an electrically conductive material.

8. The apparatus of claim 7, wherein the capillary tube is connected at an end of the capillary to the tip with a zero or low dead volume connection.

9. The apparatus of claim 1, wherein the interface comprises a capillary tube and the sheath flow interface comprises a liquid sheath layer and a gas sheath layer flowing coaxially along the capillary tube.

10. The apparatus of claim 7, wherein the sheath flow interface comprises a liquid sheath layer and a gas sheath layer flowing coaxially along the tip, the tip being connected to the capillary tube.

11. The apparatus of claim 1, wherein the means to apply voltages to said electrodes comprises a power supply.

12. The apparatus of claim 1, wherein the mass spectrometer is configured to conduct MS/MS analysis of ions from the electrospray source.

13. The apparatus of claim 1, wherein the mass spectrometer is configured to conduct mass to charge analysis ions from the electrospray sources.

14. The apparatus of claim 12, wherein during operation the power supply is electrically floating.

15. The apparatus of claim 1, further comprising a chromatographic column placed before or after the at least one channel.

16. A method for analyzing molecules, comprising:

capturing molecules traveling in an electrolyte flow stream using an electrocapture device comprising at least one anode and at least one cathode in electrical contact with the flow stream but separated by a conductive ion selective semi-permeable membrane;

releasing the captured molecules from the electrocapture device to an electrospray source via an interface between the electrocapture device and the electrospray source;

electrospraying the molecules released from the electrocapture device using the electrospray source to form gas phase ionized molecules; and analyzing the ionized molecules using a mass spectrometer, wherein said interface comprises a capillary and capturing and electrospraying of said molecules comprises co-axially flowing a liquid and a gas along said capillary.

17. The method of claim 16, further comprising separating the molecules released from the electrocapture device.

18. The method of claim 16, wherein the molecules are separated in one or more liquid chromatography columns.

19. The method of claim 16, wherein analyzing the ionized molecules comprises performing a mass to charge analysis of the ionized molecules.

20. The method of claim 16, wherein analyzing the ionized molecules comprises performing a MS/MS analysis of the ionized molecules.

21. The method of claim 16, wherein the capturing is performed using buffers of low conductivity and/or using solutions with organic solvents.

22. The method of claim 16, wherein the electrospraying is performed by spraying from a tip coated with an electrically conductive material.

\* \* \* \* \*

UNITED STATES PATENT AND TRADEMARK OFFICE
CERTIFICATE OF CORRECTION

PATENT NO.         : 8,237,117 B2
APPLICATION NO.    : 13/038012
DATED              : August 7, 2012
INVENTOR(S)        : Juan Astorga-Wells Page 1 of 1

It is certified that error appears in the above-identified patent and that said Letters Patent is hereby corrected as shown below:

Title page, column 2, Item [57], line 6, delete "base" and insert --based--, therefor.

Title page, column 2, Item [57], line 11, delete "types" and insert --types of--, therefor.

Title page, column 2, Item [57], line 14, delete "spectrometrometers." and insert --spectrometers.--, therefor.

In the Claims:

Column 4, line 40 (claim 3), delete "claims" and insert --claim--, therefor.

Column 4, line 42 (claim 4), delete "claims" and insert --claim--, therefor.

Signed and Sealed this
Twenty-first Day of May, 2013

Teresa Stanek Rea
*Acting Director of the United States Patent and Trademark Office*